(12) United States Patent
York

(10) Patent No.: US 9,371,289 B2
(45) Date of Patent: Jun. 21, 2016

(54) PHENOXYETHYL DIHYDRO-1H-ISOQUINOLINE COMPOUNDS

(71) Applicant: Eli Lilly and Company, Indianapolis, IN (US)

(72) Inventor: Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/888,497

(22) PCT Filed: May 9, 2014

(86) PCT No.: PCT/US2014/037416
§ 371 (c)(1),
(2) Date: Nov. 2, 2015

(87) PCT Pub. No.: WO2014/186218
PCT Pub. Date: Nov. 20, 2014

(65) Prior Publication Data
US 2016/0052889 A1 Feb. 25, 2016

Related U.S. Application Data

(60) Provisional application No. 61/824,436, filed on May 17, 2013.

(51) Int. Cl.
C07D 217/26 (2006.01)
A61K 31/472 (2006.01)

(52) U.S. Cl.
CPC .................................. C07D 217/26 (2013.01)

(58) Field of Classification Search
None
See application file for complete search history.

(56) References Cited

U.S. PATENT DOCUMENTS

| 7,705,035 | B2 | 4/2010 | Boyd |
| 8,642,768 | B2 | 2/2014 | Blanco-Pillado |
| 8,962,659 | B2 | 2/2015 | Schiffler |
| 2005/0250818 | A1 | 11/2005 | Koike |
| 2011/0136887 | A1 | 6/2011 | Yuan |
| 2014/0005225 | A1 | 1/2014 | Illig |
| 2015/0126555 | A1 | 5/2015 | Schiffler |

FOREIGN PATENT DOCUMENTS

| GB | 1538482 | 1/1979 |
| WO | WO9602509 | 2/1996 |
| WO | WO03041641 | 5/2003 |
| WO | WO2005021508 | 3/2005 |
| WO | WO2005105732 | 11/2005 |
| WO | WO2005105733 | 11/2005 |
| WO | WO2007121578 | 11/2007 |
| WO | WO2007143825 | 12/2007 |
| WO | WO2011102149 | 8/2011 |
| WO | WO2013004290 | 1/2013 |
| WO | WO2013004291 | 1/2013 |

*Primary Examiner* — Zinna Northington Davis
(74) *Attorney, Agent, or Firm* — Nelson L. Lentz

(57) ABSTRACT

The present invention provides a compound of the Formula I: wherein R is H or F; or a pharmaceutically acceptable salt thereof.

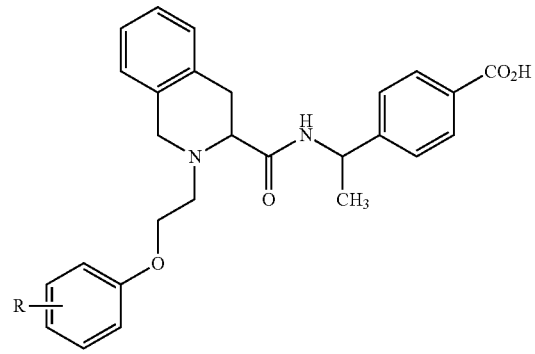

Formula I

11 Claims, No Drawings

PHENOXYETHYL DIHYDRO-1H-ISOQUINOLINE COMPOUNDS

The present invention relates to novel phenoxyethyl dihydro-1H-isoquinoline compounds, to pharmaceutical compositions comprising the compounds, to methods of using the compounds to treat physiological disorders, and to intermediates and processes useful in the synthesis of the compounds.

The present invention is in the field of treatment of inflammatory conditions, slid as arthritis, including osteoarthritis and rheumatoid arthritis, and further including pain associated with these conditions. Arthritis affects millions of people in the United States alone and is a leading cause of disability. In addition, arthritis is recognized as a significant cause of disability in companion animals. Treatments often include NSAIDs (nonsteroidal anti-inflammatory drugs) or COX-2 inhibitors, which may produce untoward cardiovascular and/or gastrointestinal side effects in patients. As such, certain patients may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3 and EP4. It has been disclosed that EP4 is the primary receptc involved in joint inflammatory pain in rodent models of rheumatoid arthritis and osteoarthritis. Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors.

WO 2013/004290 discloses cyclic amine derivatives as EP4 receptor antagonists. US 2005/0250818 discloses certain ortho substituted aryl and heteroaryl amide compounds that are EP4 receptor selective antagonists with analgesic activity. In addition, WO 2011/102149 discloses certain compounds that are selective EP4 antagonists which are useful in treating IL-23 mediated diseases.

The present invention provides certain novel compounds that are selective inhibitors of EP4 relative to EP1, EP2, and EP3. In addition, the present invention provides certain novel compounds with the potential for reduced cardiovascular or gastrointestinal side effects in comparison to traditional NSAIDs.

Accordingly, the present invention provides a compound of the Formula I:

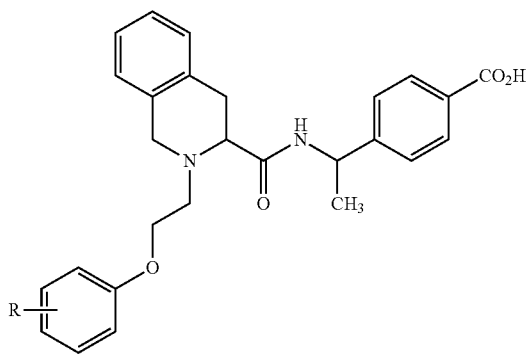

Formula I wherein R is H or F;
or a pharmaceutically acceptable salt thereof.

The present invention also provides a method of treating arthritis in a patient, comprising administering to a patient in need of such treatment an effective amount of a compound of Formula I, or a pharmaceutically acceptable salt thereof. The present invention further provides a method of treating osteoarthritis in a patient, comprising administering to a patient in need of such treatment an effective amount of a compound of Formula I, or a pharmaceutically acceptable salt thereof. In addition, the present invention provides a method of treating rheumatoid arthritis in a patient, comprising administering to a patient in need of such treatment an effective amount of a compound of Formula I, or a pharmaceutically acceptable salt thereof. The present invention also provides a method of treating pain associated with arthritis in a patient, comprising administering to a patient in need of such treatment an effective amount of a compound of Formula I, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I, or a pharmaceutically acceptable salt thereof.

Furthermore, the invention provides a compound of Formula I or a pharmaceutically acceptable salt thereof for use in therapy, in particular for the treatment of osteoarthritis. In addition, the invention provides a compound of Formula I or a pharmaceutically acceptable salt thereof for use in the treatment of rheumatoid arthritis. The invention also provides a compound of Formula I, or pharmaceutically acceptable salt thereof for use in the treatment of pain associated with osteoarthritis or rheumatoid arthritis. Furthermore, the invention provides the use of a compound of Formula I, or a pharmaceutically acceptable salt thereof, for the manufacture of a medicament for the treatment of osteoarthritis. The invention provides the use of a compound of Formula I, or a pharmaceutically acceptable salt thereof, for the manufacture of a medicament for the treatment of rheumatoid arthritis. The present invention also provides the use of a compound of Formula I, or a pharmaceutically acceptable salt thereof, for the manufacture of a medicament for the treatment of pain associated with osteoarthritis or rheumatoid arthritis.

The invention further provides a pharmaceutical composition comprising a compound of Formula I, or a pharmaceutically acceptable salt thereof, with one or more pharmaceutically acceptable carriers, diluents, or excipients. In a particular embodiment, the composition further comprises one or more other therapeutic agents. The invention also provides a pharmaceutical composition for treating arthritis comprising the compound of Formula I, or a pharmaceutically acceptable salt thereof. This invention also encompasses novel intermediates and processes for the synthesis of the compound of Formula I, or a pharmaceutically acceptable salt thereof.

As used herein, the terms "treating" or "to treat" includes restraining, slowing, stopping, or reversing the progression or severity of an existing symptom or disorder.

As used herein, the term "patient" refers to a mammal which includes a human, a companion animal, such as a cat or a dog, or a livestock animal, such as a horse, cow, or pig. Humans and companion animals are preferred patients.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, for example, Remington: The Science and Practice of Pharmacy (D. B. Troy, Editor, 21st Edition, Lippincott, Williams & Wilkins, 2006).

The compounds of the presention invention are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

The compound of Formula Ia:

Formula Ia

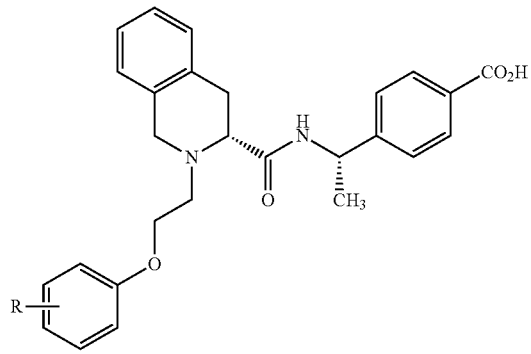

or pharmaceutically acceptable salt thereof, is preferred. In addition, the compound of Formula Ib:

Formula Ib

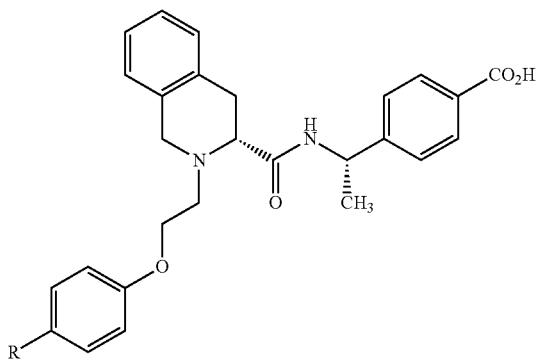

or pharmaceutically acceptable salt thereof, is preferred.

An especially preferred compound is 4-[(1S)-1-[[(3R)-2-(2-phenoxyethyl)-3,4-dihydro-1H-isoquinoline-3-carbonyl]amino]ethyl]benzoic acid, which is:

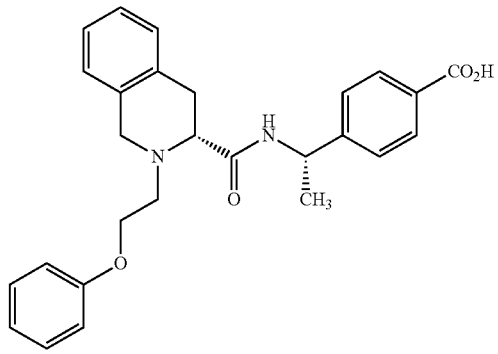 [SMILES: C[C@H](NC(=O)[C@H]1Cc2ccccc2CN1CCOc1ccccc1)c1ccc(C(=O)O)cc1]

or a pharmaceutically acceptable salt thereof.

4-[(1S)-1-[[(3R)-2-(2-Phenoxyethyl)-3,4-dihydro-1H-isoquinoline-3-carbonyl]amino]ethyl]benzoic acid is most preferred.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of Formula I by methods such as selective crystallization techniques, or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). Alternatively, suitable and readily available chiral starting materials may also be utilized as appreciated by one of ordinary skill in the art. Additionally, intermediates described in the following schemes contain nitrogen protecting groups. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

As used herein, "kPag" refers to kilopascals gauge; "Pg" refers to a suitable protecting group; "DMEM" refers to Dulbecco's Modified Eagle's Medium; "Boc" refers to a tert-butoxy carbonyl protecting group; "DMSO" refers to dimethylsulfoxide; "THF" refers to tetrahydrofuran; "EtOAc" refers to ethyl acetate; "Et$_2$O" refers to diethyl ether; "TBME" refers to tert-butyl methyl ether; "BOP" refers to benzotriazol-1-yloxytris(dimethylamino)phosphonium hexafluorophosphate; "PGE$_2$" refers to prostaglandin E$_2$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl]ethanesulfonic acid); "HTRF" refers to homogeneous time-resolved fluorescence technology; "HEK" refers to human embryonic kidney; "HBSS" refers to Hank's Balanced Salt Solution; "EC$_{80}$" refers to the concentration of an agent that produces 80% of the maximal efficacy possible for that agent; and "IC$_{50}$" refers to the concentration of an agent that produces 50% of the maximal inhibitory response possible for that agent.

The compounds of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compound of Formula I, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

Scheme 1

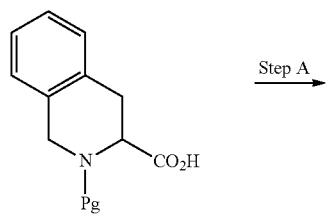

-continued

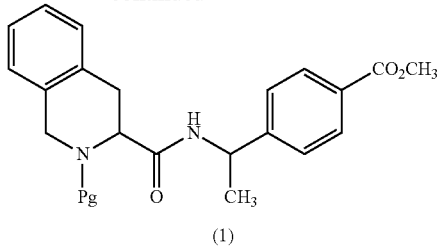

In Scheme 1, step A, a protected 3,4-dihydro-1H-isoquinoline-3-carboxylic acid, wherein Pg is a suitable nitrogen protecting group, such as a tert-butoxy carbonyl protecting group (BOC), is coupled with methyl 4-(1-aminoethyl)benzoate under standard conditions to provide the protected isoquinoline amide of structure (1). For example, the protected 3,4-dihydro-1H-isoquinoline-3-carboxylic acid is dissolved in a suitable organic solvent, such as dichloromethane, cooled to about 0° C., and treated with about 1.1 equivalents of a suitable organic base, such as triethylamine. Then about 1.1 equivalents of isobutyl chloroformate are added dropwise with stirring. The mixture is allowed to stir for about 20 minutes at 0° C., followed by addition of about 1.1 equivalents of the methyl 4-(1-aminoethyl)benzoate. The reaction mixture is then stirred for about 1 hour at room temperature. The protected isoquinoline amide (1) is then isolated using methods well known in the art, such as extraction techniques. For example, water is added to the mixture, the layers are separated, and the organic phase is washed with aqueous potassium bisulfate, followed by aqueous sodium bicarbonate. The organic phase is then dried over anhydrous magnesium sulfate, filtered, and concentrated under reduced pressure to provide the protected isoquinoline amide (1).

Scheme 2

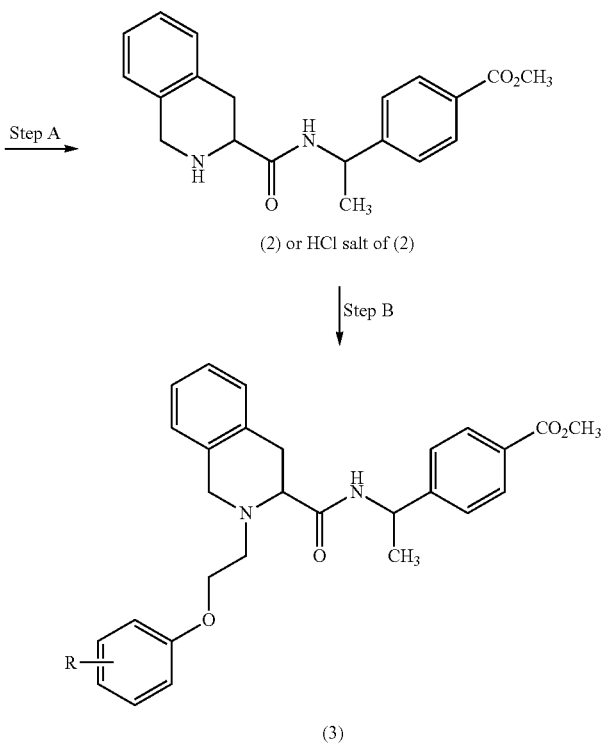

In Scheme 2, step A, the protected isoquinoline amide (1) is deprotected under conditions well known in the art to provide the deprotected isoquinoline amide (2). For example, about 10 equivalents of acetyl chloride is added dropwise to about 11 equivalents of ethanol dissolved in a suitable organic solvent, such as ethyl acetate at about 0° C. The mixture is stirred for about 30 minutes, warmed to room temperature and then a solution of about 1 equivalent of the protected isoquinoline amide (1) in ethyl acetate is added to the reaction mixture with stirring. The reaction mixture is then stirred at about 40° C. for about 12 hours. It is then cooled to room temperature and the deprotected isoquinoline is isolated using techniques well known in the art. For example, the solid is collected by filtration and dried under reduced pressure. Water is added to the solid followed by addition of 32% aqueous ammonia until the pH of the mixture reaches about 10. The solids are again collected by filtration and dried under reduced pressure at about 45° C. to provide the deprotected isoquinoline amide (2).

Alternatively, in Scheme 2, step A, the protected isoquinoline amide (1) can be deprotected under conditions well known in the art to provide the HCl salt of the deprotected isoquinoline amide (2). For example, the protected isoquinoline amide (1) is dissolved in a 4 M solution of hydrogen chloride in 1,4-dioxane. The reaction is stirred for about 12 hours at room temperature. The HCl salt of the deprotected isoquinoline amide (2) is then isolated by concentrating the reaction mixture under reduced pressure.

In Scheme 2, step B, the deprotected isoquinoline amide (2) is coupled with a suitably substituted phenoxy compound to provide the phenoxyethyl isoquinoline (3). For example, silica gel is combined with a suitable organic solvent, such as dichloromethane at about 22° C., and a solution of about 2 equivalents of sodium periodate in water is added dropwise to the stirring silica gel mixture. The mixture is stirred for about 30 minutes, and about 1.5 equivalents of 3-phenoxy-1,2-propanediol is added. The mixture is stirred for about another 30 minutes, then filtered to remove solids, the layers are separated, and the organic layer is dried over magnesium sulfate. The organic layer is again filtered and about 1 equivalent of the deprotected isoquinoline amide (2) is added followed by about 2 equivalents of a suitable reducing agent, such as sodium triacetoxyborohydride in portions. The reaction mixture is then allowed to stir for about one hour followed by addition of excess water. An aqueous solution of 32% ammonia is added to the mixture until the pH of the aqueous layer reaches about 10.

The phenoxyethyl isoquinoline (3) is then isolated and purified by techniques well know in the art. For example, the layers of the reaction mixture are separated, the organic layer is dried over magnesium sulfate, filtered, and concentrated under reduced pressure. The crude oil is dissolved in a suitable organic solvent, such as TBME, water is added, followed by 1M aqueous HCl. The resulting slurry is stirred for about 30 minutes and then concentrated under reduced pressure to remove the organic solvent. The precipitate is then collected by filtration and added to a mixture of water and TBME. The mixture is treated with 32% aqueous ammonia under the pH of the aqueous layer reaches about 10, the layers are separated, and the organic layer is washed with saturated aqueous sodium chloride, dried over magnesium sulfate, filtered, and concentrated under reduced pressure. The resulting crude material is purified by flash chromatography on silica gel with a suitable eluent, such as ethyl acetate/hexanes to provide the purified phenoxyethyl isoquinoline (3).

Alternatively, in Scheme 2, step B, the HCl salt of the deprotected isoquinoline amide (2) can coupled with a suitably substituted phenoxy compound to provide the phenoxyethyl isoquinoline (3). For example, about 1.5 equivalents of a 2-phenoxyacetaldehyde, such as 2(4-fluorophenoxy)acetaldehyde, is combined with about 1 equivalent of the HCl salt of the deprotected isoquinoline amide (2) in a suitable organic solvent, such as 1,2-dichloroethane. To this mixture is added about 1.4 equivalents of a suitable reducing agent, such as sodium triacetoxyborohydride and the reaction mixture is stirred for about 12 hours at room temperature. Saturated aqueous sodium bicarbonate is then added to the reaction mixture and the phenoxyethyl isoquinoline (3) is isolated and purified by techniques well know in the art. For example, the reaction mixture is extracted with a suitable organic solvent, such as ethyl acetate, the organic extracts are combined, washed with saturated aqueous sodium chloride, dried over magnesium sulfate, filtered, and concentrated under reduced pressure. The crude material is then purified by flash chromatography on silica gel with a suitable eluent, such as ethyl acetate/hexanes to provide the purified phenoxyethyl isoquinoline (3).

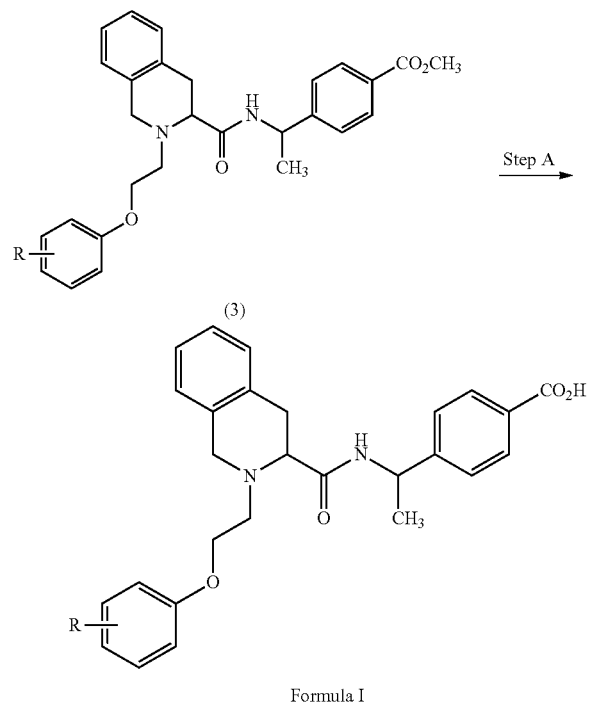

Scheme 3

In Scheme 3, step A, the phenoxyethyl isoquinoline (3) is hydrolyzed under conditions well known in the art to provide the compound of Formula I. For example, the phenoxyethyl isoquinoline (3) is dissolved in a suitable organic solvent, such as THF, or a mixture of methanol/THF, and then treated with about 2 to 4 equivalents of a suitable aqueous base, such as aqueous sodium hydroxide. The reaction is then stirred at a temperature of about 20° C. to about 40° C. for about 12 hours. The compound of Formula I is then isolated and purified under conditions well known in the art. For example, the reaction mixture is concentrated under reduced pressure to remove the organic solvent. Water is added and the aqueous layer is washed with a suitable organic solvent, such as TBME. The aqueous layer is then cooled to about 5° C. and treated with a suitable aqueous acid, such as hydrochloric acid, with stirring, until the pH reaches about 2. The reaction is then warmed to room temperature and the solids collected by filtration. The solids are then added to water, heated to about 80° C. for about one hour, cooled to room temperature, collected by filtration, and dried under reduced pressure at about 45° C. for about 12 hours. The dried solid is then added to a suitable organic solvent, such as isopropyl acetate and stirred for about 5 hours. The solids are collected by filtration and dried under reduced pressure to provide the purified compound of Formula I.

Pharmaceutically acceptable salts and common methodology for preparing them are well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One skilled in the art of synthesis will appreciate that the compounds of the present invention may be converted to and may be isolated as a pharmaceutically acceptable salt using techniques and conditions well known to one of ordinary skill in the art.

PREPARATIONS AND EXAMPLES

The following preparations and examples further illustrate the invention. Unless noted to the contrary, the compounds illustrated herein are named and numbered using Accelrys Draw (IUPAC name).

Preparation 1

Synthesis of tert-butyl (3R)-3-[[(1S)-1-(4-methoxycarbonylphenyl)ethyl]carbamoyl]-3,4-dihydro-1H-isoquinoline-2-carboxylate

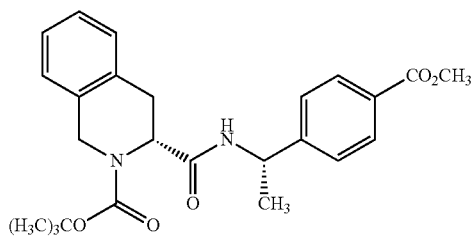

Scheme 1, Step A: To a 0° C. mixture of (3R)-2-tert-butoxycarbonyl-3,4-dihydro-1H-isoquinoline-3-carboxylic acid (40.0 g, 141.4 mmol) and dichloromethane (784 mL), add triethylamine (21.7 mL, 155.5 mmol). Then add isobutyl chloroformate (20.3 mL, 155.5 mmol) in a dropwise fashion. After the end of the addition, stir the mixture at 0° C. for 20 minutes. Then, add methyl (S)-4-(1-aminoethyl)benzoate (27.9 g, 155.5 mmol), and stir the mixture at room temperature for 1 hour. Add water (400 mL), separate the layers, and wash the organic layer with 1 M aqueous $KHSO_4$ (500 mL), followed by saturated aqueous $NaHCO_3$ (500 mL). Dry the organic phase over $MgSO_4$, filter to remove the solids, and concentrate the filtrate under reduced pressure to furnish the title compound as a white solid (60 g, 97% yield). Mass spectrum (m/z): 339 ([M+H−Boc]⁺), 383 ([M+H−t-Bu]⁺), 439 ([M+H]⁺).

Preparation 2

Synthesis of methyl 4-[(1S)-1-[[(3R)-1,2,3,4-tetrahydroisoquinoline-3-carbonyl]amino]ethyl]benzoate

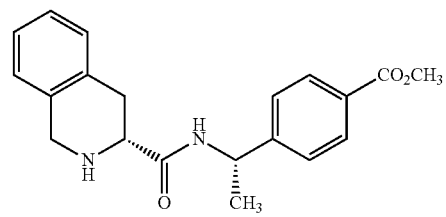 [SMILES: COC(=O)c1ccc([C@H](C)NC(=O)[C@H]2Cc3ccccc3CN2)cc1]

Scheme 2, Step A: Cool a mixture of ethyl acetate (214 mL) and ethanol (87.6 mL, 1.51 mol) to 0° C., and then add acetyl chloride (97.4 mL, 1.37 mol) in a dropwise fashion. Stir the mixture for 30 minutes while allowing it to warm to room temperature. Add a solution of tert-butyl (3R)-3-[[(1S)-1-(4-methoxycarbonylphenyl)ethyl]carbamoyl]-3,4-dihydro-1H-isoquinoline-2-carboxylate (60 g, 137 mmol) in ethyl acetate (480 mL), and then stir the resulting mixture at 40° C. overnight. Cool the mixture to room temperature, then isolate the resulting precipitate by filtration, and dry under reduced pressure. Add water (300 mL) to the solid, and then add a 32% aqueous ammonia solution until the pH of the mixture reaches 10. Isolate the suspended solids by filtration, then dry them in a vacuum oven at 45° C. overnight to furnish the title compound as a white solid (44 g, 95% yield). Mass spectrum (m/z): 339 ([M+H]⁺), 677 ([2M+H]⁺), 699 ([2M+Na]⁺).

Preparation 3

Synthesis of methyl 4-[(1S)-1-[[(3R)-2-(2-phenoxyethyl)-3,4-dihydro-1H-isoquinoline-3-carbonyl]amino]ethyl]benzoate

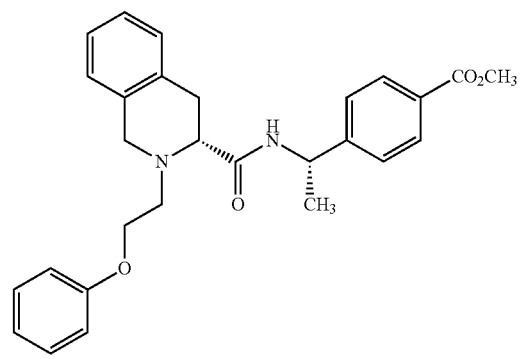 [SMILES: COC(=O)c1ccc([C@H](C)NC(=O)[C@H]2Cc3ccccc3CN2CCOc2ccccc2)cc1]

Scheme 2, Step B: To a stirring mixture of silica gel (200 g, 3.33 mol) and dichloromethane (1100 mL) at 22° C., add a solution of sodium periodate (56.2 g, 260 mmol) in water (352 mL) in a dropwise fashion. After the end of the addition, stir the mixture for an additional 30 minutes, then add 3-phenoxyl-1,2-propanediol (34.5 g, 195 mmol), resulting in a slight exotherm. Stir the mixture for an additional 30 minutes, then filter to remove the solids, discard the aqueous layer, and dry the organic layer over $MgSO_4$, filter to remove the solids, and treat the filtrate with methyl 4-[(1S)-1-[[(3R)-1,2,3,4-tetrahydroisoquinoline-3-carbonyl]amino]ethyl]benzoate (44 g, 130 mmol). Then, add sodium triacetoxyborohydride (57.4 g, 260 mmol) in small portions. Upon completion of the addition, stir the mixture for one additional hour, then add water (200 mL). Add a 32% aqueous ammonia solution until the pH of the aqueous layer reaches 10. Separate the layers, dry the organic layer over MgSO$_4$, filter to remove the solids, and concentrate the filtrate under reduced pressure. Dissolve the resulting crude oil in TBME (300 mL), then add water (250 mL) and 1 M aqueous hydrochloric acid (200 mL). Stir the resulting slurry for 30 minutes, concentrate under reduced pressure to remove the TBME, and isolate the resulting white precipitate by filtration. Pour this precipitate into a stirring mixture of water (400 mL) and TBME (400 mL), and add a 32% aqueous ammonia solution until the pH of the aqueous layer reaches 10. Remove the aqueous layer, and wash the organic layer with a saturated aqueous sodium chloride solution (200 mL). Isolate the organic layer, dry over MgSO$_4$, filter to remove the solids, and concentrate under reduced pressure. Subject the resulting crude material to flash chromatography on silica gel using a 30% to 70% EtOAc/hexanes gradient. Consolidate the fractions containing the product, and concentrate them under reduced pressure to furnish the title compound as a white solid (44 g, 74% yield). Mass spectrum (m/z): 459 ([M+H]$^+$).

Preparation 4

Synthesis of methyl 4-[(1S)-1-[[(3R)-1,2,3,4-tetrahydroisoquinoline-3-carbonyl]amino]ethyl]benzoate hydrochloride

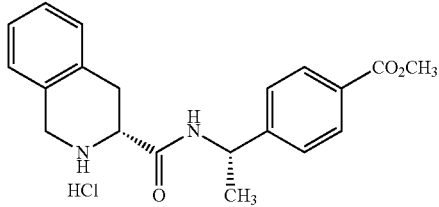 [SMILES: COC(=O)c1ccc([C@H](C)NC(=O)[C@H]2Cc3ccccc3CN2)cc1 ; Cl]

Scheme 2, Step A: Dissolve tert-butyl (3R)-3-[[(1S)-1-(4-methoxycarbonylphenyl)ethyl]carbamoyl]-3,4-dihydro-1H-isoquinoline-2-carboxylate (5.5 g, 12.5 mmol) in a 4 M solution of hydrogen chloride in 1,4-dioxane (30 mL, 120 mmol). Stir the mixture overnight at room temperature, and then concentrate the mixture under reduced pressure to furnish the title compound as a white solid (4.70 g, 100% yield). Mass spectrum (m/z): 339 ([M+H]$^+$), 677 ([2M+H]$^+$), 699 ([2M+Na]$^+$).

Preparation 5

Synthesis of methyl 4-[(1S)-1-[[(3R)-2-(2-(4-fluorophenoxy)ethyl)-3,4-dihydro-1H-isoquinoline-3-carbonyl]amino]ethyl]benzoate

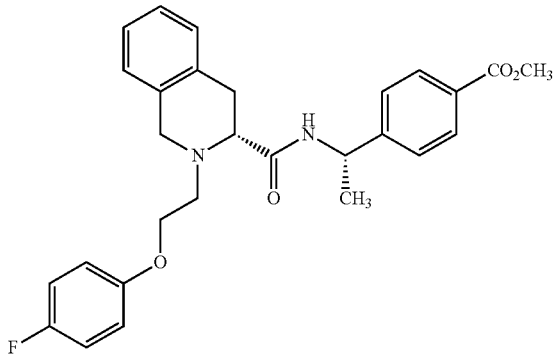 [SMILES: COC(=O)c1ccc([C@H](C)NC(=O)[C@H]2Cc3ccccc3CN2CCOc2ccc(F)cc2)cc1]

Scheme 2, Step B: To a mixture of methyl 4-[(1S)-1-[[(3R)-1,2,3,4-tetrahydroisoquinoline-3-carbonyl]amino]ethyl]benzoate hydrochloride (800 mg, 2.13 mmol) and 2-(4-fluorophenoxy)acetaldehyde (493 mg, 3.2 mmol) in 1,2-dichloroethane (10.7 mL), add sodium triacetoxyborohydride (633 mg, 2.99 mmol) and stir the mixture at room temperature overnight. Add saturated aqueous NaHCO$_3$ (25 mL), and extract the aqueous layer with ethyl acetate (2×25 mL). Wash the combined organic layers with saturated aqueous NaCl (25 mL), dry the organic phase over MgSO$_4$, filter, and concentrate the filtrate under reduced pressure. Subject the resulting crude material to flash chromatography on silica gel using a 0% to 60% EtOAc/hexanes gradient. Consolidate the fractions containing the product, and concentrate them under reduced pressure to furnish the title compound as a colorless foam (550 mg, 54% yield). Mass spectrum (m/z): 477 ([M+H]$^+$).

EXAMPLE 1

Synthesis of 4-[(1S)-1-[[(3R)-2-(2-phenoxyethyl)-3,4-dihydro-1H-isoquinoline-3-carbonyl]amino]ethyl]benzoic acid

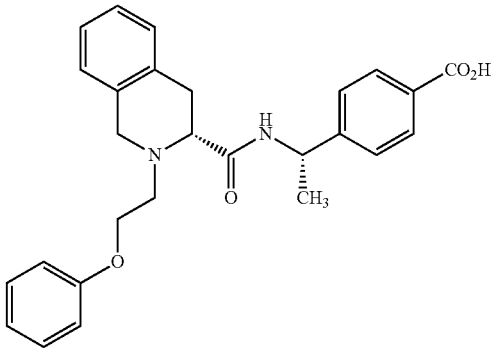 [SMILES: C[C@H](NC(=O)[C@H]1Cc2ccccc2CN1CCOc1ccccc1)c1ccc(C(=O)O)cc1]

Scheme 3, Step A: Stir a mixture of methyl 4-[(1S)-1-[[(3R)-2-(2-phenoxyethyl)-3,4-dihydro-1H-isoquinoline-3-carbonyl]amino]ethyl]benzoate (41.5 g, 90.5 mmol), THF (291 mL), and 2 M aqueous sodium hydroxide (181 mL, 360 mmol) at 40° C. overnight. Concentrate under reduced pressure to remove the THF. Add water (200 mL), then wash the aqueous layer with TBME (2×200 mL). Cool the aqueous layer to 5° C. and add concentrated aqueous hydrochloric acid with stirring until the pH reaches 2 (as estimated by pH paper analysis). With stirring, allow the mixture to warm to room temperature over 30 minutes, then isolate the solids by filtration. Add the solids to water (500 mL) and heat to 80° C. for one hour. Cool the mixture to room temperature, isolate the solids by filtration, and dry the solids in a vacuum oven at 45° C. overnight. Add the solids to isopropyl acetate (300 mL) and stir vigourously for 5 h. Isolate the solids by filtration, and dry the solids under reduced pressure to furnish the title compound as a white solid (26 g, 60% yield). Mass spectrum (m/z): 445 ([M+H]$^+$).

Example 2

Synthesis of 4-[(1S)-1-[[(3R)-2-(2-(4-fluorophenoxy)ethyl)-3,4-dihydro-1H-isoquinoline-3-carbonyl]amino]ethyl]benzoic acid hydrochloride

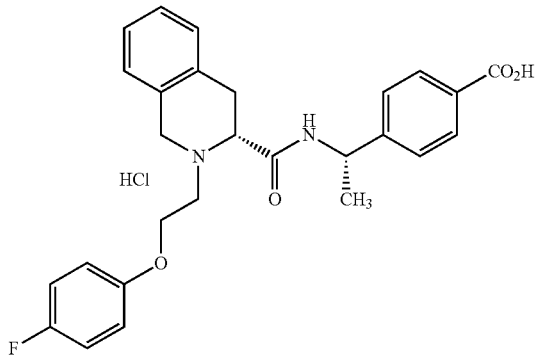 [SMILES: C[C@H](NC(=O)[C@H]1Cc2ccccc2CN1CCOc1ccc(F)cc1)c1ccc(C(=O)O)cc1 ; Cl]

Scheme 3, Step A: Dissolve methyl 4-[(1S)-1-[[(3R)-2-(2-(4-fluorophenoxy)ethyl)-3,4-dihydro-1H-isoquinoline-3-carbonyl]amino]ethyl]benzoate (550 mg, 1.15 mmol) in a mixture of methanol (10 mL) and tetrahydrofuran (10 mL). Add a 5 N aqueous solution of sodium hydroxide (0.462 mL, 2.31 mmol), then stir the mixture at room temperature overnight. Concentrate the mixture under reduced pressure to furnish a white solid. Add a 4 M solution of hydrogen chloride in 1,4-dioxane (10 mL, 40 mmol), and stir the mixture at room temperature for 10 min Remove the suspended solids by filtration, rinsing the solids with THF (5 mL). Concentrate the combine filtrate under reduced pressure to furnish a white solid. Triturate the material in hot diethyl ether (10 mL), and filter to furnish the title compound as a white solid (535 mg, 93% yield). Mass spectrum (m/z): 463 ([M+H]$^+$), 485 ([M+Na]$^+$).

In Vitro Binding to Human EP1, EP2, EP3 and EP4 hEP1 and hEP4 membranes are prepared from recombinant HEK293 cells stably expressing the human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer (see e.g., Mauback, K. A., *British Journal of Pharmacology*, 156: 316-327 (2009)) contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

$K_d$ values for [$^3$H]-PGE$_2$ binding to each receptor are determined by saturation binding studies or homologous competition. Compounds are tested in a 96-well format using a three-fold dilution series to generate a 10-point curve. Diluted compound is incubated with 20 μg/well EP1, 10 μg/well EP2, 1 ug/well EP3 or 10 to 20 μg/well EP4 membrane for 90 minutes at 25° C. in the presence of 0.3 to 0.5 nM [$^3$H]-PGE$_2$ (PerkinElmer, 118 to 180 Ci/mmol). The binding reaction is performed in 200 μL MES buffer (10 mM MES pH 6.0 with KOH, 10 mM MgCl$_2$ and 1 mM EDTA) using 0.5 mL polystyrene 96-well deep-well plates. Nonspecific binding is calculated by comparing binding in the presence and absence of 2 μM of PGE$_2$. The membranes are harvested by filtration (TomTek harvester), washed 4 times with cold buffer (10 mM MES pH 6.0 with KOH, 10 mM MgCl$_2$), dried in a 60° C. oven, and the radioactivity is quantified as counts per minute (CPM) using a TopCount® detector. Percent specific binding is calculated as the percent of the binding in the absence of any inhibitor, corrected for non-specific binding in the presence of 2 μM of PGE$_2$. Data are analyzed using a 4-parameter nonlinear logistic equation (ABase Equation 205) as shown: y=(A+((B−A)/(1+((C/x)^D)))) where, y=% specific inhibition, A=bottom of the curve; B=top of the curve; C=relative IC$_{50}$=concentration causing 50% inhibition based on the range of the data from top to bottom; D=Hill Slope=slope of the curve. K$_i$ conversion from IC$_{50}$ Values (K$_i$=IC$_{50}$/(1+[L]/K$_d$) where [L] is the ligand concentration).

TABLE 1

| | In vitro binding of Examples 1 and 2 to human EP1, EP2, EP3 and EP4 | | | |
|---|---|---|---|---|
| Test Compound | hEP1, K$_i$ (nM) | hEP2, K$_i$ (nM) | hEP3, K$_i$ (nM) | hEP4, K$_i$ (nM) |
| Ex. 1 | 7920 ± 5810 (n = 3) | 1320 ± 1780 (n = 4) | >14800 (n = 3) | 0.403 ± 0.247 (n = 9) |
| Ex. 2 | 4650 (n = 1) | 331 ± 72 (n = 2) | >14600 (n = 1) | 0.380 ± 0.142 (n = 4) |

The compounds are tested following the procedures essentially as described above. The data in Table 1 demonstrate that the compounds of Example 1 and Example 2 bind to hEP4 at sub-nanomolar concentrations. The data in Table 1 also demonstrate the compounds of Example 1 and Example 2 bind to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 μg/mL geneticin and 2 mM L-glutamine. Confluent cultures are grown at 37° C. in an atmosphere containing 5% CO$_2$. Cells are harvested using 0.25% Trypsin-EDTA, suspended in freeze media (FBS with 6% DMSO) at 10$^7$ cells/mL and aliquots are stored in liquid nitrogen. Just before assay, cells are thawed in DMEM, centrifuged, and resuspended in cAMP buffer.

The inhibition of PGE$_2$-stimulated cAMP production by EP4 antagonists is measured using HTRF (Cisbio catalogue #62AM4PEB). An aliquot equivalent to 4000 cells is incubated with 50 μL cAMP assay buffer containing PGE$_2$ in a concentration predetermined to produce an EC$_{80}$ (0.188 nM PGE$_2$ from Sigma, catalog # P5640-10 mg) and EP4 antagonists at room temperature for 20 minutes. cAMP assay buffer contains 500 mL HBSS, 0.1% BSA, 20 mM HEPES and 200 μM IBMX (Sigma I5879). CJ-042794 serves as a positive control (see WO 2005/021508, example 68, 4-{(1S)-1-[({5- chloro-2-[(4-fluorophenyl)oxy]phenyl}carbonyl)amino]ethyl}benzoic acid; see also Murase, A., et al., *Life Sciences*, 82:226-232 (2008)). To measure the cAMP levels, cAMP-d2 conjugate and anti cAMP-cryptate conjugate in lysis buffer are incubated with the treated cells at room temperature for 1 hour. The HTRF signal is detected using an EnVision plate reader (Perkin-Elmer) to calculate the ratio of fluorescence at 665 nm to that at 620 nm. The raw data are converted to cAMP amount (pmol/well) using a cAMP standard curve generated for each experiment. Data are analyzed using a 4-parameter nonlinear logistic equation (ABase Equation 205) as shown: $y=(A+4B-A)/(1+((C/x)^D))))$ where, y=% specific inhibition, A=Bottom of the curve, B=Top of the curve, C=Relative $IC_{50}$=concentration causing 50% inhibition based on the range of the data from top to bottom, D=Hill, Slope=slope of the curve.

The compounds are tested following the procedures essentially as described above. The compound of Example 1 has an $IC_{50}$ of 0.752±0.538 nM (n=12) and the compound of Example 2 has an $IC_{50}$ of 0.450±0.256 nM (n=4) measured at human EP4. This demonstrates that the compounds of Example 1 and Example 2 are antagonists of human EP4 in vitro.

In Vitro Rat EP4 Functional Antagonist Activity

Rat EP4 cDNA (Genebank Accession# NM_03276) is cloned into pcDNA 3.1 vector and subsequently transfected in HEK293 cells for receptor expression. Rat EP4 stable clone is scaled up and then frozen down as cell bank for future compounds screening. To test EP4 antagonist compounds in rEP4 cells, thaw the frozen cells and then resuspend cells in cAMP assay buffer. The cAMP buffer is made by HBSS without Phenol Red (Hyclone, SH30268) supplemented with 20 mM HEPES (Hyclone, SH30237), 0.1% BSA (Gibco, 15260) and 125 µM IBMX (Sigma, 15879) (see e.g., Murase, A., et al., *Life Sciences*, 82:226-232 (2008)). The cells are plated into 96-well half area flat-bottom polystyrene black plates (Costar 3694). Compounds are serial diluted with DMSO to give 10-point concentration response curves. Then diluted compounds are added into cAMP assay buffer which contains $PGE_2$ (Cayman 14010, in a concentration predetermined to produce an $EC_{80}$) at ratio of DMSO/buffer at 1/100. The cells are treated with compounds in the presence of $PGE_2$ ($EC_{80}$ concentration) for 30 minutes at room temperature. The cAMP levels generated from the cells are quantified by a cAMP HTRF assay kit (Cisbio 62AM4PEC). The plates are read on an EnVision plate reader using HTRF optimized protocol (PerkinElmer). $IC_{50}$s are calculated using Graphpad Prism (v. 4) nonlinear regression, sigmoidal dose response curve fitting.

The compounds are tested following the procedures essentially as described above. The compound of Example 1 has an $IC_{50}$ of 2.0 nM (n=1) and the compound of Example 2 has an $IC_{50}$ of 6.7 nM (n=1) measured at rat EP4. This demonstrates that the compounds of Example 1 and Example 2 are antagonists of rat EP4 in vitro.

In Vitro Antagonist Activity in Human Whole Blood

The inhibitory effects of $PGE_2$ on LPS-induced TNFα production from macrophages/monocytes are believed to be mediated by EP4 receptors (See Murase, A., et al., *Life Sciences*, 82:226-232 (2008)). The ability of the compound of Example 1 to reverse the inhibitory effect of $PGE_2$ on LPS-induced TNFα production in human whole blood is an indicia of functional activity.

Blood is collected from normal volunteer donors into sodium heparin vacutainer tubes. Donors have not taken NSAIDs or celecoxib within 48 hours or glucocorticoids within two weeks prior to the donation. All tubes/donor are pooled into 50 mL Falcon conical centrifuge tubes and 98 µL/well is distributed into 96-well tissue culture plates (Falcon 3072). Compounds are diluted into DMSO to 100×final and 1 µL/well in triplicate is added to the blood to give 7-point concentration response curves. The blood is pretreated with the compounds at 37° C., in a 5% $CO_2$ humidified atmosphere, for 30 minutes, after which 1 µL/well of a solution of 1 mg/mL of lipopolysaccharide (LPS) (Sigma 0111:B4) in 0.2 mg/mL bovine serum albumin (BSA)/PBS both with and without 1 mM $PGE_2$ (Cayman 14010) is added to give a final LPS concentration of 10 µg/mL both with and without 10 nM $PGE_2$. The plates are incubated for 20-24 hours at 37° C. in a 5% $CO_2$, humidified atmosphere. The plates are centrifuged at 1800×g for 10 minutes at 22° C., in an Eppendorf 5810R centrifuge. Plasma is removed from the cell layer and is transferred to v-bottom polypropylene plates. TNFα levels in 2 µL plasma are quantified by a commercially available enzyme immunoassay (R&D Systems DY210), using Immulon 4 HBX plates (Thermo 3855) and 3,3',5,5' tetramethylbiphenyl-4,4'-diamine substrate (KPL 50-76-03). The plates are read at $A_{450}$-$A_{650}$ on a plate reader (Molecular Devices Versamax) using SOFTmaxPRO (v. 4.3.1) software. $IC_{50}$s are calculated using Graphpad Prism (v. 4) nonlinear regression, with sigmoidal dose response curve fitting. Results are expressed as the geometric mean±standard deviation; n=number of independent determinations.

The compounds are tested following the procedures essentially as described above. The compound of Example 1 has an $IC_{50}$ of 39±21 nM (n=8) and Example 2 has an $IC_{50}$ of 61±55 nM (n=5) measured at human EP4. This demonstrates that the compounds of Example 1 and Example 2 are EP4 antagonists in the human blood TNFα induction assay.

I Claim:

1. A compound of the formula:

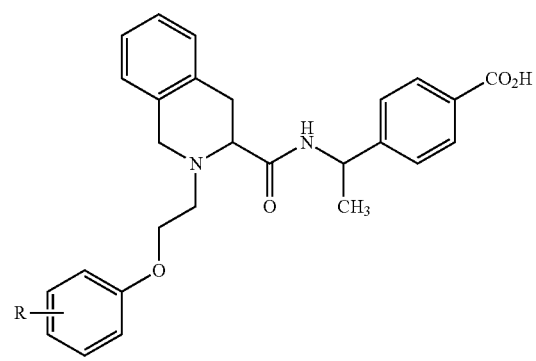

wherein R is H or F;

or a pharmaceutically acceptable salt thereof.

2. The compound or salt according to claim 1 which is:

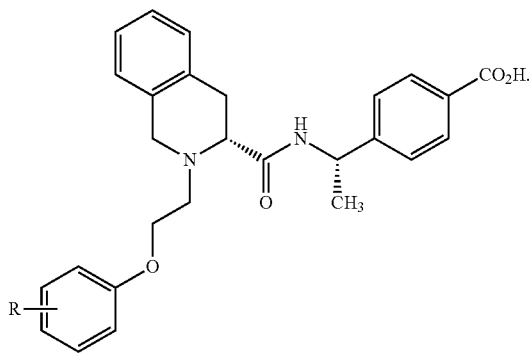

3. The compound or salt according to claim 2 which is:

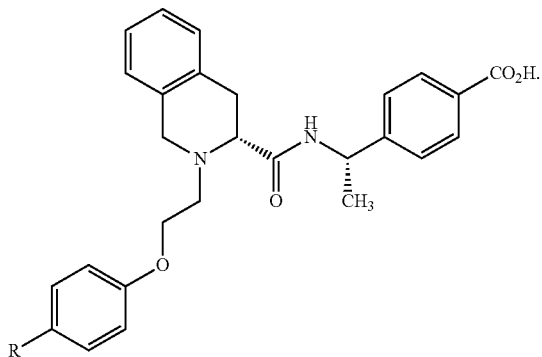

4. The compound according to claim 3 which is 4-[(1S)-1-[[(3R)-2-(2-phenoxyethyl)-3,4-dihydro-1H-isoquinoline-3-carbonyl]amino]ethyl]benzoic acid:

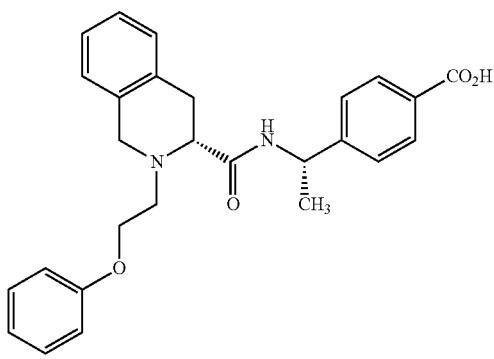 [SMILES: C[C@H](NC(=O)[C@H]1Cc2ccccc2CN1CCOc1ccccc1)c1ccc(C(=O)O)cc1]

or a pharmaceutically acceptable salt thereof.
5. The compound according to claim 4 which is 4-[(1S)-1-[[(3R)-2-(2-phenoxyethyl)-3,4-dihydro-1H-isoquinoline-3-carbonyl]amino]ethyl]benzoic acid:

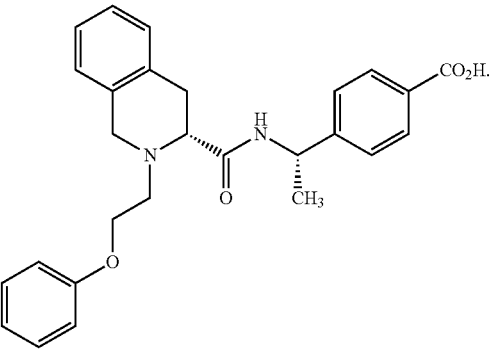 [SMILES: C[C@H](NC(=O)[C@H]1Cc2ccccc2CN1CCOc1ccccc1)c1ccc(C(=O)O)cc1]

6. The compound according to claim 3 which is 4-[(1S)-1-[[(3R)-2-(2-(4-fluorophenoxy)ethyl)-3,4-dihydro-1H-isoquinoline-3-carbonyl]amino]ethyl]benzoic acid:

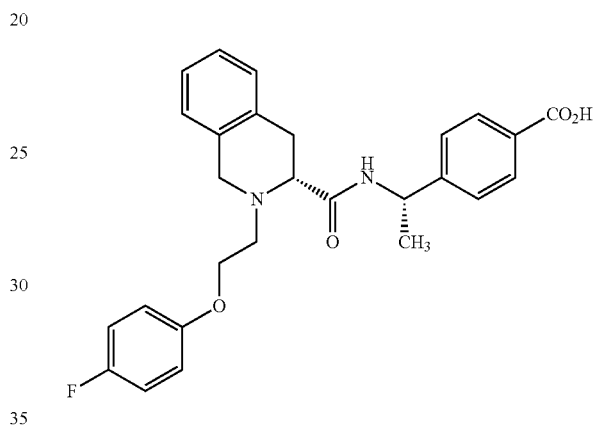

or a pharmaceutically acceptable salt thereof.

7. A method of treating osteoarthritis in a patient, comprising administering to a patient in need of such treatment an effective amount of a compound, or pharmaceutically acceptable salt thereof, according to claim 1.

8. A method of treating rheumatoid arthritis in a patient, comprising administering to a patient in need of such treatment an effective amount of a compound, or pharmaceutically acceptable salt thereof, according to claim 1.

9. A method of treating pain associated with osteoarthritis or rheumatoid arthritis in a patient, comprising administering to a patient in need of such treatment an effective amount of a compound, or a pharmaceutically acceptable salt thereof, according to claim 1.

10. A pharmaceutical composition, comprising a compound or a pharmaceutically acceptable salt thereof according to claim 1 with one or more pharmaceutically acceptable carriers, diluents, or excipients.

11. A pharmaceutical composition, comprising a compound or a pharmaceutically acceptable salt thereof according to claim 4 with one or more pharmaceutically acceptable carriers, diluents, or excipients.

* * * * *